United States Patent
Aga et al.

(10) Patent No.: US 7,880,483 B2
(45) Date of Patent: Feb. 1, 2011

(54) METHOD FOR INSPECTING QUALITY OF CORE MATERIAL FOR ELECTROPHOTOGRAPHIC FERRITE CARRIER

(75) Inventors: Koji Aga, Chiba (JP); Hiromichi Kobayashi, Chiba (JP)

(73) Assignee: Powdertech Co., Ltd., Chiba (JP)

( * ) Notice: Subject to any disclaimer, the term of this patent is extended or adjusted under 35 U.S.C. 154(b) by 289 days.

(21) Appl. No.: 12/057,530

(22) Filed: Mar. 28, 2008

(65) Prior Publication Data
US 2008/0238450 A1    Oct. 2, 2008

(30) Foreign Application Priority Data
Mar. 30, 2007   (JP) ............... 2007-094761

(51) Int. Cl.
*G01R 27/08* (2006.01)
(52) U.S. Cl. ............... 324/693; 324/71.4; 702/26; 422/81; 430/111.4
(58) Field of Classification Search .......... 324/693
See application file for complete search history.

(56) References Cited

U.S. PATENT DOCUMENTS

| | | | |
|---|---|---|---|
| 6,548,209 B2* | 4/2003 | Fetcenko et al. ......... 429/218.1 |
| 6,582,870 B2 | 6/2003 | Kayamoto et al. |
| 2002/0127144 A1* | 9/2002 | Mehta ................. 422/81 |
| 2003/0222656 A1* | 12/2003 | Phillips et al. ............ 324/605 |
| 2004/0226404 A1* | 11/2004 | Ozaki et al. ................ 75/252 |
| 2004/0239344 A1* | 12/2004 | Hu ............................ 324/698 |
| 2006/0194137 A1 | 8/2006 | Kobayashi et al. |
| 2006/0265150 A1* | 11/2006 | Hu et al. .................... 702/50 |
| 2007/0205747 A1* | 9/2007 | Cho et al. ................. 324/71.4 |
| 2010/0159382 A1* | 6/2010 | Horie et al. ............ 430/111.32 |

FOREIGN PATENT DOCUMENTS

| | | |
|---|---|---|
| JP | 2002-296846 | 10/2002 |
| JP | 2002-357930 | 12/2002 |
| JP | 2006-235460 | 9/2006 |

OTHER PUBLICATIONS

English language Abstract of JP 2002-296846, Oct. 9, 2002.
English language Abstract of JP 2002-357930, Dec. 13, 2002.
English language Abstract of JP 2006-235460, Sep. 7, 2006.

* cited by examiner

*Primary Examiner*—Melissa J Koval
*Assistant Examiner*—Benjamin M Baldridge
(74) *Attorney, Agent, or Firm*—Greenblum & Bernstein, P.L.C.

(57) ABSTRACT

An object of the present invention is to provide a quality inspection method for obtaining a specifying factor which can more reliably indicate powder characteristics of a core material for an electrophotographic ferrite carrier. The method includes measuring an impedance of the core material for the electrophotographic ferrite carrier to obtain a Cole-Cole plot in which a real number impedance is arranged in an X-axis and an imaginary number impedance is arranged in a Y-axis, and evaluating characteristics of particles of the core material for the electrophotographic ferrite carrier using the Cole-Cole plot.

6 Claims, 7 Drawing Sheets

Fig 3

| Sample | Ferrite Carrier Composition | Evaluation Results | | | | | | | | | | |
|---|---|---|---|---|---|---|---|---|---|---|---|---|
| | | Example | | | | | | | Comparative Example | | Conventional Properties | |
| | | AC-Resistances (Impedances) | | | | | | | DC-Resistances (Gap:6.5mm) | | | |
| | | $R_1$ | CPE-$T_1$ | CPE-$P_1$ | $R_2$ | CPE-$I_2$ | CPE-$P_2$ | IRsI | R50V | R1000V | S.S.A* (m²/g) | $D_{50}$** |
| Sample 1 | Li-Mn Type | 3.0 E+06 | 6.0 E-11 | 0.89 | 6.4 E+06 | 1.3 E-09 | 0.83 | 3798 | 5.20 E+08 | 5.10 E+08 | 0.0807 | 35 |
| Sample 2 | Li-Mn Type | 4.8 E+06 | 8.2 E-11 | 0.89 | 5.4 E+06 | 2.1 E-09 | 0.81 | 5033 | 3.10 E+09 | 2.50 E+09 | 0.0807 | 35 |
| Sample 3 | Li-Mn Type | 5.4 E+06 | 2.5 E-11 | 0.85 | 9.5 E+06 | 3.5 E-09 | 0.84 | 5820 | 4.10 E+08 | 2.70 E+07 | 0.1554 | 50 |
| Sample 4 | Li-Mn Type | 3.6 E+06 | 5.1 E-11 | 0.88 | 6.2 E+06 | 1.7 E-09 | 0.83 | 5004 | 9.80 E+08 | 1.10 E+09 | 0.1829 | 35 |
| Sample 5 | Li-Mn Type | 1.3 E+06 | 7.9 E-11 | 0.87 | 2.5 E+06 | 8.6 E-09 | 0.65 | 5649 | 8.10 E+07 | 6.50 E+07 | 0.2031 | 20 |
| Sample 6 | Li-Mn Type | 4.5 E+06 | 5.4 E-11 | 0.88 | 7.5 E+06 | 1.9 E-09 | 0.83 | 9582 | 4.10 E+08 | 4.10 E+08 | 0.2759 | 35 |
| Sample 7 | Li-Mn Type | 4.5 E+06 | 5.4 E-11 | 0.88 | 7.5 E+06 | 1.9 E-09 | 0.83 | 9582 | 4.10 E+08 | 4.10 E+08 | 0.2759 | 35 |

S.S.A.*: Specific Surface Area measured by B.E.T Method
$D_{50}$**: Volume Median Diameters

Fig 4

| Sample | Ferrite Carrier Composition | Evaluation Results | | | | | | | | | | |
|---|---|---|---|---|---|---|---|---|---|---|---|---|
| | | Example | | | | | | | Comparative Example | | Conventional Properties | |
| | | AC-Resistances (Impedances) | | | | | | | DC-Resistances (Gap:6.5mm) | | | |
| | | $R_1$ | $CPE-T_1$ | $CPE-P_1$ | $R_2$ | $CPE-T_2$ | $CPE-P_2$ | $|Rs|$ | $R50V$ | $R1000V$ | S.S.A* ($m^2/g$) | $D_{50}$** |
| Sample 5 | Li-Mn Type | 1.3 E+06 | 7.9 E-11 | 0.87 | 2.5 E+06 | 8.6 E-09 | 0.65 | 5649 | 8.10 E+07 | 6.50 E+07 | 0.2031 | 20 |
| Sample 2 | Li-Mn Type | 4.8 E+06 | 8.2 E-11 | 0.89 | 5.4 E+06 | 2.1 E-09 | 0.81 | 5033 | 3.10 E+09 | 2.50 E+09 | 0.0807 | 35 |
| Sample 1 | Li-Mn Type | 3.0 E+06 | 6.0 E-11 | 0.89 | 6.4 E+06 | 1.3 E-09 | 0.83 | 3798 | 5.20 E+08 | 5.10 E+08 | 0.0807 | 35 |
| Sample 4 | Li-Mn Type | 3.6 E+06 | 5.1 E-11 | 0.88 | 6.2 E+06 | 1.7 E-09 | 0.83 | 5004 | 9.80 E+08 | 1.10 E+09 | 0.1829 | 35 |
| Sample 6 | Li-Mn Type | 4.5 E+06 | 5.4 E-11 | 0.88 | 7.5 E+06 | 1.9 E-09 | 0.83 | 9582 | 4.10 E+08 | 4.10 E+08 | 0.2759 | 35 |
| Sample 7 | Li-Mn Type | 4.5 E+06 | 5.4 E-11 | 0.88 | 7.5 E+06 | 1.9 E-09 | 0.83 | 9582 | 4.10 E+08 | 4.10 E+08 | 0.2759 | 35 |
| Sample 3 | Li-Mn Type | 5.4 E+06 | 2.5 E-11 | 0.85 | 9.5 E+06 | 3.5 E-09 | 0.84 | 5820 | 4.10 E+08 | 2.70 E+07 | 0.1554 | 50 |

S.S.A.*: Specific Surface Area measured by B.E.T Method
$D_{50}$**: Volume Median Diameters

METHOD FOR INSPECTING QUALITY OF CORE MATERIAL FOR ELECTROPHOTOGRAPHIC FERRITE CARRIER

BACKGROUND OF THE INVENTION

1. Field of the Invention

The present invention relates to a method for inspecting a quality of a core material for an electrophotographic ferrite carrier which is used together with a toner to be used in an electrophotographic developing device such as a copying machine.

2. Description of the Related Art

A core material for an electrophotographic ferrite carrier is a ferrite particle having a shape represented by an approximately sphere, and is handled as a ferrite powder which is gathered ferrite particles. Accordingly, an evaluation method applied to a powder has been widely applied to the quality evaluation method of the core material.

To provide a carrier for an electrophotographic developer which enables to prevent the carrier scattering and to give a high-grade picture quality, and the electrophotographic developer using the carrier, Patent Document 1 (Japanese Patent Laid-Open No. 2002-296846) discloses to adopt the carrier for the electrophotographic developer comprising that a volume median diameter ($D_{50}$) of spherical core materials of a magnetic carrier is 25 to 45 μm; an average void size of carrier particles is 10 to 20 μm; particles with a particle size of 22 μm or smaller obtained by a volumetric particle size distribution measurement is less than 1%; the magnetization intensity in a magnetic field of 1 KOe is 67 to 88 emu/g; and a difference of magnetization intensity between the scattered particles and the remainder in the magnetic field of 1 KOe is 10 emu/g or less. It means that the patent specifies the carrier for the electrophotographic developer which can prevent the carrier scattering and can provide the high-grade picture quality by using characteristics of the volumetric particle size distribution (volume median diameter ($D_{50}$)), the average void size, and the magnetization characteristics.

Next, Patent Document 2 (Japanese Patent Laid-Open No. 2002-357930) discloses a carrier for an electrophotographic developer, which shows an adequate flowability in a developing machine and on a sleeve without deposition in the machine, scattering of a toner and fogging. And it enables to obtain a high picture quality showing high image density and a superior repetition for narrow lines and dots for a long period of time. The carrier for the electrophotographic developer employs a carrier for an electrophotographic developer having specific characteristics that a fluidity index (F1) shown by the expression of "F1=AD×FR" is 63 to 75 sec/(50·cm³), and a fluidity index (F2) shown by the expression of "F2=AD×Hc" is 30 to 100 Oe·g/cm³. In addition, the Patent Document 2 discloses that saturation magnetization in an applied magnetic field of 3,000 Oe is preferably 20 to 45 emu/g. In Patent Document 2, AD represents apparent density (g/cm³), FR represents a flow rate (sec/50 g), and Hc (Oe) represents a coercive force. It means that in Patent Document 2, factors of the fluidity index, the apparent density, the flow rate, the coercive force, and the saturation magnetization is used for specifying the carrier for the electrophotographic developer.

Furthermore, object of Patent Document 3 (Japanese Patent Laid-Open No. 2006-235460) is to provide a ferrite carrier core material of an irregular shape, which has reduced electric resistance, large specific surface area, low density and long life. And the electrophotographic developer using the core material of the ferrite carrier enables to prevent a toner scattering, and can support up speed and colorization with high image density. In order to achieve the object, the Patent Document 3 adopts the core materials with irregular shapes of the ferrite carrier and 40% or more by the number of core materials have a rock type crystal sugar shape and/or an oyster shell shape, having a shape factor (SF−1=$R^2$/S×π/4×100, wherein R represents a maximum length and S represents an area) of 140 to 250 with a distribution width (δ) of 60 or less. The Patent Document 3 also discloses other factors of apparent density, a specific surface area, an average particle size, saturation magnetization and resistance with the most suitable range for the respective factors. It means that in Patent Document 3, all of these specifying factors are used for specifying the carrier for the electrophotographic developer.

As described above, the specifying factors above have been generally used to specify a core material for a ferrite carrier for an electrophotographic developer of good quality. The specifying factors could generally show good performance.

However, the materials may sometimes not perform a quality aimed even when the respective core materials of the ferrite carrier qualify specific ranges of characteristics disclosed in respective Patent Documents. This is because that the core material generally has a deviation of the quality in a certain level as long as the core material of the ferrite carrier is an industrial product.

For instance, it is supposed that there are two types of products having definitely different surface states when particles of the core material of a ferrite carrier for the electrophotographic developer are observed with an electron microscope. In such a case, the two types of products can have almost the same characteristics of a volumetric particle size distribution (volume median diameter ($D_{50}$)), an average void size and magnetization characteristics, which are the specifying factors used in Patent Document 1. In the case, a product that cannot achieve a purpose of Patent Document 1, preventing the carrier scattering and providing a high-grade picture quality may exist and is a disclosure of the quality deviation in the products.

There also be an actuality, for instance, that difference exists between the surface state of particles which can be judged from the image of the core material which is observed on the electrophotographic ferrite carrier by a scanning electron microscope and the surface state of particles which can be judged from specific surface area measured by a BET method. The above described specific surface area measured by a BET method is often used as an evaluation index for the surface state of the core material for the electrophotographic ferrite carrier. However, as a size of a particle is reduced, the dependency of specific surface area to the particle size tends to increase and specific surface area increases. On the other hand, bubbles and caves (parts considered not to be completely connected to surface) contained in particles of the core material for the electrophotographic ferrite carrier cannot be measured. Accordingly, the specific surface area measured by a BET method cannot be an index showing the state of pores in a bulk part of the core material for the electrophotographic ferrite carrier. Because a BET method to measure the specific surface area should be used for inspecting the specific surface area of a particle having 1 m²/g or larger, so the BET method has not sufficient accuracy for inspecting the particle such as the core material, having a comparatively small specific surface area. In addition, a volume median diameter ($D_{50}$) measured by a laser diffraction scattering analysis method is an average value in a particle size distribution showing cumulative particle sizes of a certain volumes of particles. As a result, it may fluctuate largely depending on the accuracy of measurement for the particle size distribution. In contrast, an observed image by using a scanning electron microscope or an analysis method on the image can make us understand the surface state of each particle, but those method cannot make us judge the level of a surface property of the whole particles constituting a powder as the core material for the electrophotographic ferrite carrier.

As described above, it has been required to search additional specifying factors that enables to demonstrate the powder characteristics of the core material of the ferrite carrier more reliably and precisely other than the conventional specifying factors for the core material of the ferrite carrier used in the above described Patent Documents.

SUMMARY OF THE INVENTION

Accordingly, the present inventors made an extensive investigation and find out that conventional evaluation methods or specifying factors for a core material of a ferrite carrier for an electrophotographic developer are evaluating the core material of the ferrite carrier for the electrophotographic developer as a whole. Then, the present inventors conceived that the deviation of products of the core material of the ferrite carrier for the electrophotographic developer could be reduced if a state of each particle of the core material of the ferrite carrier for the electrophotographic developer could be separately examined from a state of the particles as a powder. As a result, the present inventors found out a method for inspecting the quality of a core material for the electrophotographic ferrite carrier according to the present invention. The present invention will be described below.

A method for inspecting the quality of a core material for an electrophotographic ferrite carrier according to the present invention is characterized in that the impedance of the core material for the electrophotographic ferrite carrier is measured by using an AC-resistance measuring method to obtain a Nyquist diagram (Cole-Cole plot) in which a real number impedance (Z') is arranged in an X-axis and an imaginary number impedance (Z") is arranged in a Y-axis and then the characteristics of the particles of the core material for the electrophotographic ferrite carrier is evaluated by using the Nyquist diagram (Cole-Cole plot).

In the method for inspecting the quality of the core material for the electrophotographic ferrite carrier, the Nyquist diagram (Cole-Cole plot) is obtained by changing the frequency of the current applied in the AC-resistance measurement in the range of 0.01 Hz to 1 MHz.

In the method for inspecting the quality of a core material for the electrophotographic ferrite carrier according to the present invention, it is preferable to evaluate the state of each particle of a core material for the electrophotographic ferrite carrier by using a parameter obtained from the Nyquist diagram (Cole-Cole plot).

In the method for inspecting the quality of a core material for the electrophotographic ferrite carrier according to the present invention, it is preferable to judge the quality of the core material for the electrophotographic ferrite carrier by using the value of the parameters one or two or more in combination selected from $|Rs|$, $Rp_1$, $CPE-T_1$, $CPE-P_1$, $Rp_2$, $CPE-T_2$ and $C PE-P_2$, which are AC-resistance values (including constant) obtained when the impedance of the carrier particles is measured by using an AC-resistance measuring method according to an equivalent circuit expressed by Expression 3 that will be described later.

In the method for inspecting the quality of the core material for the electrophotographic ferrite carrier according to the present invention, it is preferable to use $CPE-P_1$ mainly as a parameter for evaluating the state of each particle of the core material for the electrophotographic ferrite carrier.

In the method for inspecting the quality of the core material for the electrophotographic ferrite carrier according to the present invention, it is preferable to judge the quality of the core material for the electrophotographic ferrite carrier by using a relationship between a time constant $\tau_1$ which indicates the state of the each particle and a time constant $\tau_2$ which indicates the state of the particles as a powder, both are given in the Nyquist diagram (Cole-Cole plot).

It is also preferable to use the time constants, $\tau_1$ which indicates the state of the particles in the vicinity of the surface and is expressed by $\tau_1 = Rp_1 \times (CPE-T_1)$, and $\tau_2$ which indicates the state of the particles as the powder and is expressed by $\tau_2 = Rp_2 \times (CPE-T_2)$.

ADVANTAGES OF THE INVENTION

In the method for inspecting the quality of a core material for an electrophotographic ferrite carrier according to the present invention, an AC-resistance measurement enables to get information on the state of every particles of the core material for the electrophotographic ferrite carrier and the state of the particles as a powder simultaneously and separately. Accordingly, the method can be used as an index for independently judging the state of every particles and the state of the particles as the powder. As a result, the method enables to select the core material for the electrophotographic ferrite carrier at a higher level which a conventional method has never achieved when the method of the present invention is used in combination with specifying factors described in the above described Patent Documents. As a result, the core material for the electrophotographic ferrite carrier which performance is matched to the characteristics of electrophotographic developing devices such as a copying machine can be selected.

BRIEF DESCRIPTION OF THE DRAWINGS

FIG. 3 is a table for comparing values in AC-resistance measurement in Example 1, DC-resistance measurement in Comparative examples and specific surface areas measured by a BET method to recognize relationship among them;

FIG. 4 is a table for comparing values of AC-resistance measurement in Example 1, DC-resistance measurement in Comparative examples and volume median diameter ($D_{50}$) to recognize relationship among them;

DETAILED DESCRIPTION OF THE PREFERRED EMBODIMENTS

An embodiment of a method for inspecting the quality of a core material for an electrophotographic ferrite carrier according to the present invention will be described. First procedure for inspecting the quality of the core material for the electrophotographic ferrite carrier according to the present invention is inspection of the impedance of the core material for the electrophotographic ferrite carrier by using an AC-resistance measuring method and obtaining a Nyquist diagram (Cole-Cole plot) which arranges real number impedance (Z') in an X-axis and arranges imaginary number impedance (Z") in a Y-axis.

At first, a frequency of a current to be applied in the above described AC-resistance measuring method according to the present invention will be described. The frequency of the current to be applied in the AC-resistance measurement is changed preferably in the range of 0.01 Hz to 1 MHz to obtain the Nyquist diagram (Cole-Cole plot). It is preferable to select and apply the frequency in a wide range of 0.01 Hz to 1 MHz to obtain the Nyquist diagram (Cole-Cole plot) and then calculate each response factor (parameters) by using the Nyquist diagram (Cole-Cole plot). This is because it is difficult to precisely calculate the required parameters when a narrow frequency range of 10 Hz to 100 kHz is applied in the measurement.

Next, a reason why the AC-resistance measuring method was employed will be described. A core material for an electrophotographic ferrite carrier is a powder composed of particles mainly formed of iron oxide. When a DC-resistance of such a powder is measured by using a direct current, the measured value cannot be an index for the surface property of particles, because the value is greatly affected by the composition and a particle size of the core material for the electrophotographic ferrite carrier. In contrast, the AC-resistance measuring method can measure impedance while changing the frequency of the current. In addition, the index for the surface property of particles can be obtained by examining an electric response obtained in the impedance measurement. Furthermore, specifically, when a high-frequency electric field is applied to a sample (here, it is the core material for the electrophotographic ferrite carrier), a response factor which has a short relaxation time can follow well to the change of the electric field. On the other hand, a response factor with a long relaxation time cannot follow the change of the electric field, because a reversed electric field is applied to the core material for the electrophotographic ferrite carrier before the electric current flows therein. As a result, the AC-resistance measurement can extract the response factor with the short relaxation time and the response factor with the long relaxation time independently.

Figure 1:
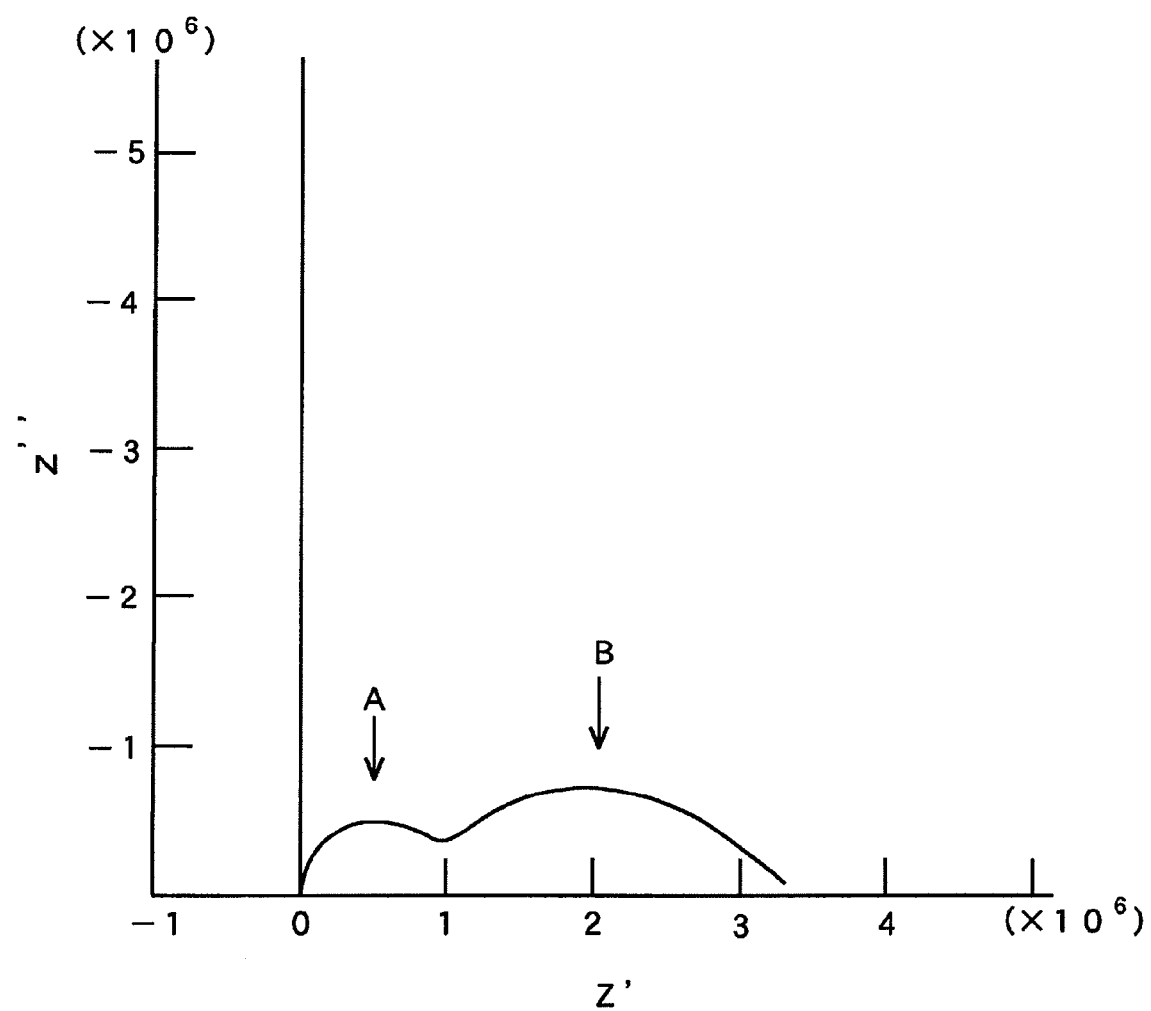
FIG. 1 is one of Nyquist diagrams (Cole-Cole plot) obtained by measuring the impedance of a powder of a core materials for an electrophotographic ferrite carrier.

As for the core material for the electrophotographic ferrite carrier, the response factor with the short relaxation time can be considered to correspond to the response factor including the information on each particle of the core material for the electrophotographic ferrite carrier, and the response factor with the long relaxation time can be considered to correspond to the response factor including information as a powder of the core material for the electrophotographic ferrite carrier. FIG. 1 shows one of examples of a Nyquist diagram (Cole-Cole plot) which arranges real number impedance (Z') in an X-axis and arranges imaginary number impedance (Z") in a Y-axis obtained after measuring the impedance of the core material for the electrophotographic ferrite carrier. As is clear from FIG. 1, plotted two arcs having a semicircle-like shape can be found. One of the arcs is the response factor including the information on each particle of the core material for the electrophotographic ferrite carrier, and another arc is the response factor including the information as the powder of the core material for the electrophotographic ferrite carrier. In general, a semicircle-like shape with an arrow (A) of FIG. 1 can be considered to include the information on each particle, and a semicircle-like shape with an arrow (B) can be considered to include the information as a powder. However, the semicircle-like shapes may vary depending on an AC-resistance measurement condition, because it is affected by a shape, a component or the like of the particles of the core material for the electrophotographic ferrite carrier.

If each electric response could be directly judged from a Nyquist diagram (Cole-Cole plot) as illustrated in FIG. 1, there would be no problem. However, actually, it is not easy to divide a response factor after considering on a relaxation period of time of each response factor. Thus, data analysis may be required by using a fitting technique. Accordingly, it is necessary to consider an equivalent circuit in the AC-resistance measurement of a core material for an electrophotographic ferrite carrier. In general, the equivalent circuit is considered as a so-called RC circuit in which a resistor R and a capacitor C are combined. In the equivalent circuit, the capacitance C substitutively indicates a time lag of response corresponding to the change of an electric field. However, it was empirically considered from the result of the impedance measurement of the core material for the electrophotographic ferrite carrier that it is difficult to express the equivalent circuit by using a popular RC circuit. Then, it was judged that it is preferable to extend the capacitance C to CPE (Constant Phase Element) which indicates the distortion of a semicircle-like shape in the Nyquist diagram (Cole-Cole plot) by considering the core material for the electrophotographic ferrite carrier as a substance similar to a dielectric substance. It is because that the core material is not a metal in which electrical charges are accumulated only on the particle surface but is a substance having a higher resistance than a metal, in which electrical charges are accumulated in the whole particle. As a result, an equivalent circuit shown in the following Expression 3 was adopted.

Expression 3

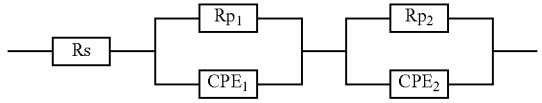

In Expression 3, Rs is a virtual resistance (resistance in which an effect of an electrode surface, static electricity and the like are considered) for reducing a deviation in calculation, and can be any of positive and negative values. Here, when CPE-T is defined as an electrostatic capacitance (F), and CPE-P is defined as an index (dimensionless) indicating a degree of a deviation from certain state, respective impedances $Z_{CPE1}$ and $Z_{CPE2}$ of $CPE_1$ and $CPE_2$ can be expressed by the following Expression 4. In Expression 4, j represents a complex number and ω represents an angular velocity.

$$Z_{CPE1} = \frac{1}{(CPE-T_1) \times (j\omega)^{CPE-P_1}},$$

$$Z_{CPE2} = \frac{1}{(CPE-T_2) \times (j\omega)^{CPE-P_2}}$$

Expression 4

A method for inspecting the quality of a core material for an electrophotographic ferrite carrier according to the present invention uses each AC-resistance value (including constant) obtained when the impedance is measured according to an equivalent circuit shown in Expression 3, for the purpose of inspecting the quality of the core material for the electrophotographic ferrite carrier. Specifically, values of the each parameters |Rs|, $Rp_1$, $CPE\text{-}T_1$, $CPE\text{-}P_1$, $Rp_2$, $CPE\text{-}T_2$ and $CPE\text{-}P_2$ are obtained by inspecting the impedance. Then, the quality of the core material for the electrophotographic ferrite carrier is judged by using the value of the parameters one or two or more in combination selected from |Rs|, $Rp_1$, $CPE\text{-}T_1$, $CPE\text{-}P_1$, $Rp_2$, $CPE\text{-}T_2$ and $CPE\text{-}P_2$.

For instance, electric characteristics obtained from the impedance measurement are included in $Rp_1$ and $CPE\text{-}T_1$ in the Expression 3. In addition, because $CPE\text{-}P_1$ is a dimensionless quantity having no unit, it is considered that $CPE\text{-}P_1$ indicates information concerning on a state of each particle of the core material for the electrophotographic ferrite carrier, even affected by a composition of the core material for the electrophotographic ferrite carrier to some extent. As a result, without consideration on the size and resistance of the particle, $CPE\text{-}P_1$ can be possibly used as an absolute evaluation index which indicates a state (which can be considered to include voids existing in bulk part of the core material for the electrophotographic ferrite carrier) of each particle of the core material for the electrophotographic ferrite carrier.

The core material for the electrophotographic ferrite carrier can be handled as a metallic oxide because it contains iron oxide as a main component. If so, the CPE-P1 can be possibly capable of evaluating a state of each particle of the core material for the electrophotographic ferrite carrier without consideration on a composition of the core material for the electrophotographic ferrite carrier. When the comparison on the values obtained in the impedance measurement on various powder characteristics according to the above assumption was made, it is possible to evaluate the characteristics of the core material for the electrophotographic ferrite carrier as a powder or as a particle which conventional evaluation methods have never achieved.

Also in general, a value of |Rs| has been likely considered to be an error component. However, in some kind of a core material for an electrophotographic ferrite carrier, the value of |Rs| may be used as an index which indicates some powder characteristic. But the concept cannot be applied to all of core materials for electrophotographic ferrite carriers, and it varies depending on measurement conditions for AC-resistance as well. Particularly, in the method for inspecting the quality of a core material for the electrophotographic ferrite carrier according to the present invention, an optimal measurement condition should be flexibly determined according to characteristics of a core material for the electrophotographic ferrite carrier which is an object to be measured, and factors to be measured. Specifically, relationship among each value obtained from AC-resistance measurement according to the above described equivalent circuit and the powder characteristics of a core material for the electrophotographic ferrite carrier which is the object to be measured should be determined according to the type of a core material for the electrophotographic ferrite carrier.

Furthermore, it is preferable to evaluate the relaxation time such as a time constant and use it positively. In the method for inspecting the quality of a core material for the electrophotographic ferrite carrier according to the present invention, the above described Nyquist diagram (Cole-Cole plot) can sometime show a time constant $\tau_1$ which indicates a state of each particle and a time constant $\tau_2$ which indicates a state of particles as a powder separately. In such a case, it is preferable to judge the quality of a core material for the electrophotographic ferrite carrier by using a relationship between the time constants. When a frequency of the current has a relationship of $\omega=2\pi f$ at a top of a semicircle-like shape of a Nyquist diagram (Cole-Cole plot) as is shown in FIG. 1 with equivalent circuit of Expression 3, the time constant $\tau_1$ which indicates the state of the particle in the vicinity of the surface is expressed by the expression of $\tau_1=Rp_1\times(CPE\text{-}T_1)$, and the time constant $\tau_2$ which indicates the state of the particles as the powder is expressed by the expression of $\tau_2=RP_2\times(CPE\text{-}T_2)$. The time constants are the relaxation time investigated when an electrical field is applied to a core material for the electrophotographic ferrite carrier while the electrical field is changed with time, so they can be used as an index which remarkably indicates the electric characteristics of a core material for the electrophotographic ferrite carrier.

The following example show one of examples obtained by measuring characteristics of a core material for an electrophotographic ferrite carrier by using an AC-resistance measuring method.

Example 1

Figure 2:
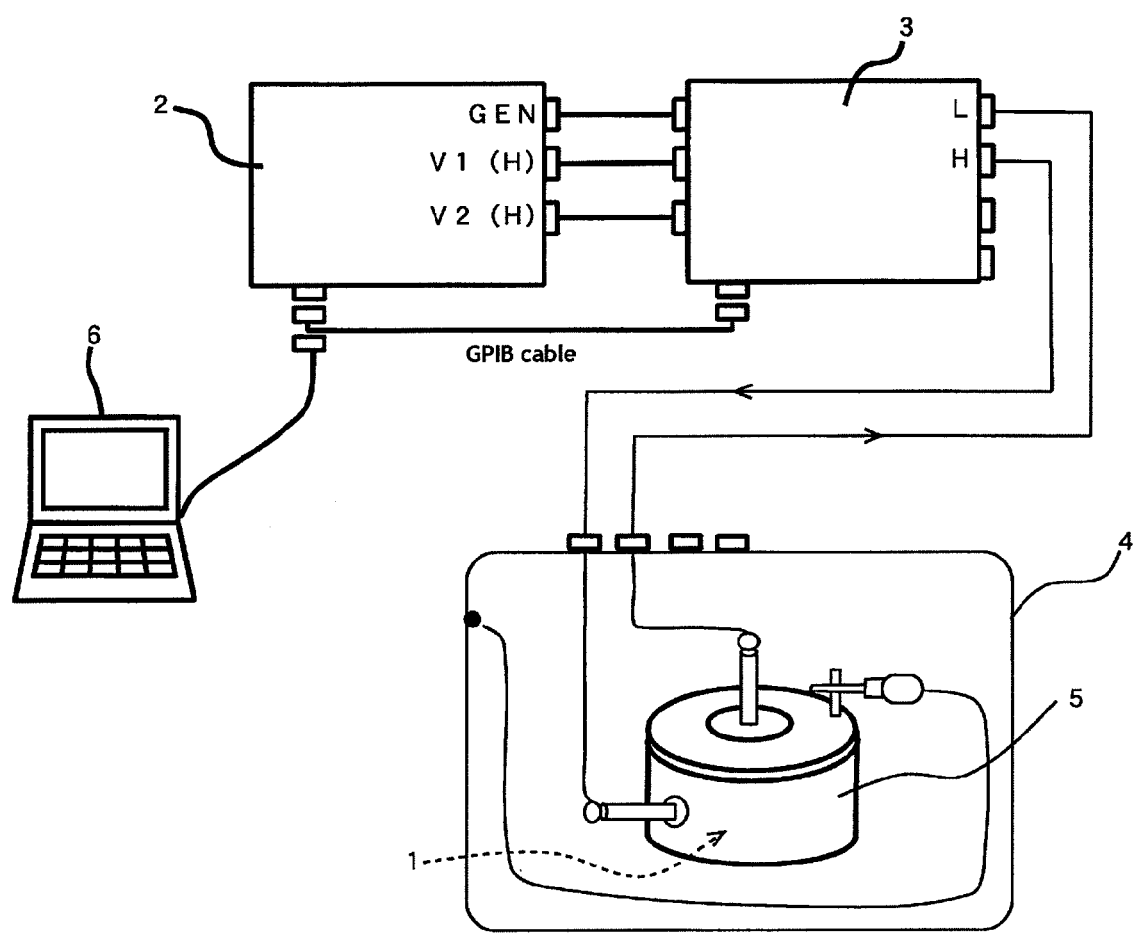
FIG. 2 is a schematic diagram illustrating a basic construction of a frequency-response analyzing instrument used for AC-resistance measurement.

Example 1 show whether there is a correlation or not between a value obtained in AC-resistance measurement and a specific surface area measured by a BET method which is a conventional measurement. The AC-resistance was measured by using a type 1260 frequency response analyzer (FRA) 2 made by Solartron Analytical (U.K.) having a basic construction illustrated in FIG. 2 connected with a type 1296 dielectric interface 3. As is shown in FIG. 2, the terminals of the type 1296 dielectric interface 3 were wired to each electrode of an input electrode, an output electrode and a guard electrode in a sample cell 5 in a shielded box 4 of the AC-resistance measuring system. In the construction, a sample 1 of a core material for an electrophotographic ferrite carrier was put in the sample cell 5 (suggested by a broken arrow in FIG. 2). The core material for the electrophotographic ferrite carrier used was the Mn—Li ferrite carrier core material which contains a certain amount of manganese and lithium. The data measured at the time was taken into a personal computer 6 shown in FIG. 2.

The personal computer 6 was arranged to automatically take the data measured into from the type 1260 frequency response analyzer (FRA) 2 through a GP-IB interface made by National Instruments Corporation. At this time, the inspecting system was controlled by using the software SMaRT.

Then the conditions for measurement will be described. An applied AC voltage was 5 V as a root-mean-square value. The frequency was swept from 1 MHz to 0.01 Hz at every six points between digits of a logarithmic scale. A sample cell used was LF-21 for liquid electrode made by Toyo Corporation, which has the electrostatic capacitance of 2 pF and the sample capacity of 1 cc. The core material for an electrophotographic ferrite carrier were prepared in the sample cell after measuring the weight to satisfy sample weight (g)=(apparent density (g/cc))×1 cc.

After finishing measurements of the characteristics of the samples of the core material for the electrophotographic ferrite carrier as described above, the characteristics of the samples were evaluated by using the analysis software ZVIEW made by Solartron Analytical (U.K.). As for the specific evaluation method, the characteristics were evaluated by setting an equivalent circuit composed of |Rs|, $Rp_1$, $CPE_1$, $RP_2$ and $CPE_2$ shown in FIG. 3, followed by performing numerical calculation (fitting) on the obtained measurement data to judge |Rs|, $Rp_1$, $CPE-T_1$, $CPE-P_1$, $Rp_2$, $CPE-T_2$ and $CPE-P_2$. On the sample in which the measured data in the above steps were far from an semicircle-like shape arc in a Nyquist diagram (Cole-Cole plot), the data was divided according to a frequency and subjecting to "instant fit" which is one of functions in the software ZVIEW to obtain value of the each parameters |Rs|, $Rp_1$, $CPE-T_1$, $CPE-P_1$, $Rp_2$, $CPE-T_2$ and $CPE-P_2$ as the values of respective parameters. The evaluation results on samples of the various core materials for an electrophotographic ferrite carrier are shown in the tables of FIG. 3 and FIG. 4. Selection of seven samples (Sample 1 to Sample 7) in which the specific surface area measured by a BET method and the volume median diameter ($D_{50}$) were considered to be approximately reliably measured were judged with the observation with an electron microscope in addition.

Comparative Example

The comparative example was performed for comparison with the above described Example 1. Resistance values (Ω) were measured by applying DC voltages of 50 V and 1,000 V to each of sample 1 to sample 7 of the core materials for an electrophotographic ferrite carrier described above. A method for inspecting the above described resistance value will be described. Specifically, the resistance value was measured by arranging two nonmagnetic plate electrodes (10 mm×40 mm) in parallel with a gap of 6.5 mm and weighed 200 mg of the sample was filled in the gap. Then the magnets (having surface inductive flux of 1,500 Gauss and area contacting with electrode of 10 mm'30 mm) were attached onto the plate electrodes to make the sample held between the electrodes, followed by sequentially applying voltages of 50 V and 1,000 V between electrodes to measure the resistance in each applied voltage with an insulation resistance tester (SM-8210 made by DKK-TOA CORPORATION). The measurement was performed in a thermo-hygrostat room with a room temperature of 25° C. and a humidity of 55%. The evaluation results on each samples of a core materials for an electrophotographic ferrite carrier are shown in tables of FIG. 3 and FIG. 4 for comparison with example 1.

Comparison Between Example 1 and Comparative Example

At first, a performance in example 1 will be described. See the table in FIG. 3. The table in FIG. 3 arranges specific surface area measured by a BET method in order of increasing value downward to examine the correlation between specific surface area measured by a BET method and values of AC-resistance measured. Values of the volume median diameter ($D_{50}$) measured at the time are also shown in the Table. As a result, it can be understood that there is a strong correlation between values of |Rs| obtained by an AC-resistance measurement and values of the specific surface area measured by a BET method. When the comparison is made against to the values of the volume median diameter ($D_{50}$), no correlation with the values of |Rs| is observed. In other words, the value of |Rs| obtained by the AC-resistance measurement enables to judge the state of each particle of the core material for an electrophotographic ferrite carrier without consideration on the particle size, and can show a good correlation with the specific surface area measured by a BET method.

Next, see the table in FIG. 4. The table in FIG. 4 arranges measured values of the volume median diameter ($D_{50}$) in order of increasing value downward to examine the correlation between the volume median diameter ($D_{50}$) and the values of AC-resistance measured. Values of the specific surface area measured by a BET method at the time are also shown in the Table. It can be understood that values of $CPE-P_2$ and values of $R_2$ obtained by the AC-resistance measurement respectively show an adequate correlation with values of the volume median diameter ($D_{50}$). In other words, respective values of $CPE-P_2$ and $R_2$ obtained by the AC-resistance measurement enables to judge the state of particles as the powder of the core material for the electrophotographic ferrite carrier without consideration on the specific surface area measured by a BET method, and can show a good correlation with the volume median diameter ($D_{50}$).

In the examination on the values of DC-resistance in comparative examples shown in FIG. 3 and FIG. 4, the values do not show correlation with any characteristic of the specific surface area measured by a BET method and the volume median diameter ($D_{50}$). Accordingly, it is clear that it is difficult to apply the DC-resistance method for evaluating powder characteristics of the core material for the electrophotographic ferrite carrier. It means that the AC-resistance measuring method should be applied.

Example 2

In the example 2, it will be described that the value obtained by AC-resistance measurement can show a state of each particle of the core material in an electrophotographic ferrite carrier, which never be shown by the value of a specific surface area measured by a BET method of a conventional measurement.

Figure 5:
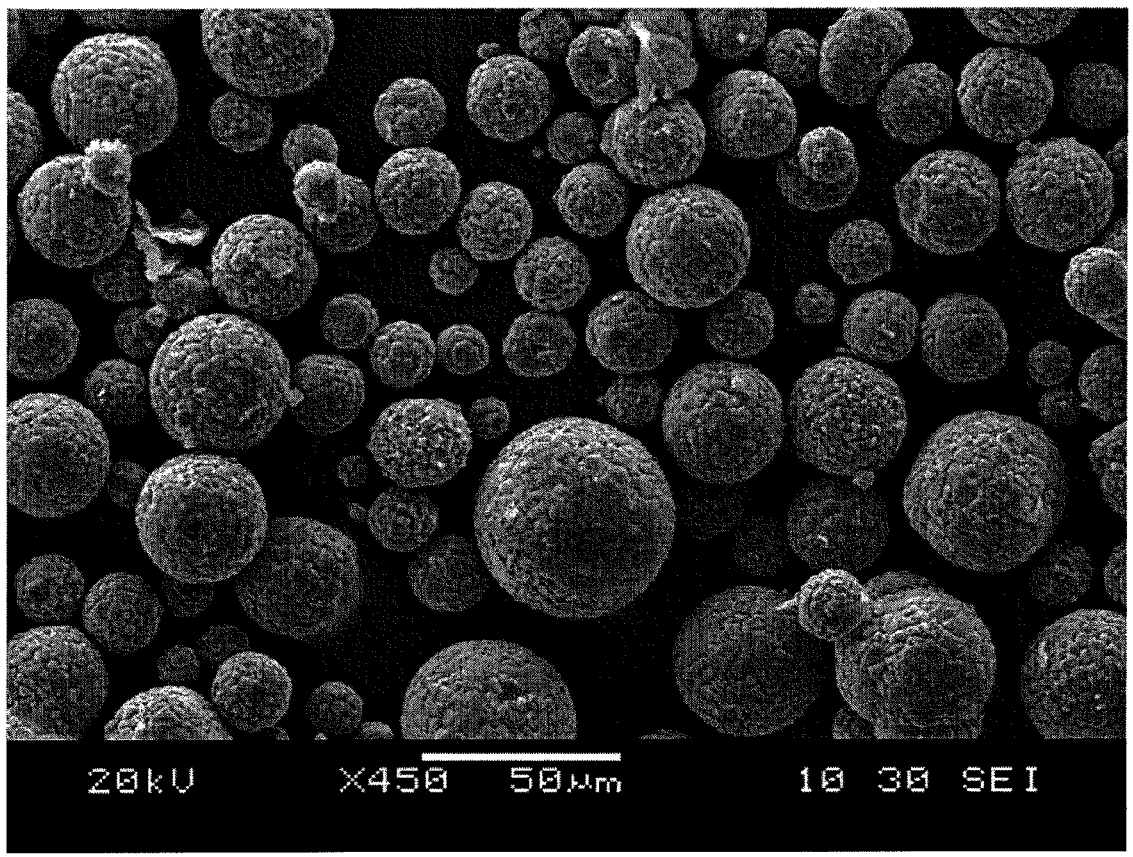
FIG. 5 is an observed image (with magnification of 450 times) of particles of a core material for an electrophotographic ferrite carrier (sample (A) in Example 2) by using a scanning electron microscope.

The sample (A) which had the volume median diameter ($D_{50}$) of 35 μm and the specific surface area of 0.08 m²/g measured by a BET method was used as a control sample. FIG. 5 shows an observation image (with magnification of 450 times) of the sample (A), which was obtained by using a scanning electron microscope. The sample (A) showed the value of 0.89 for $CPE-P_1$.

Figure 6:
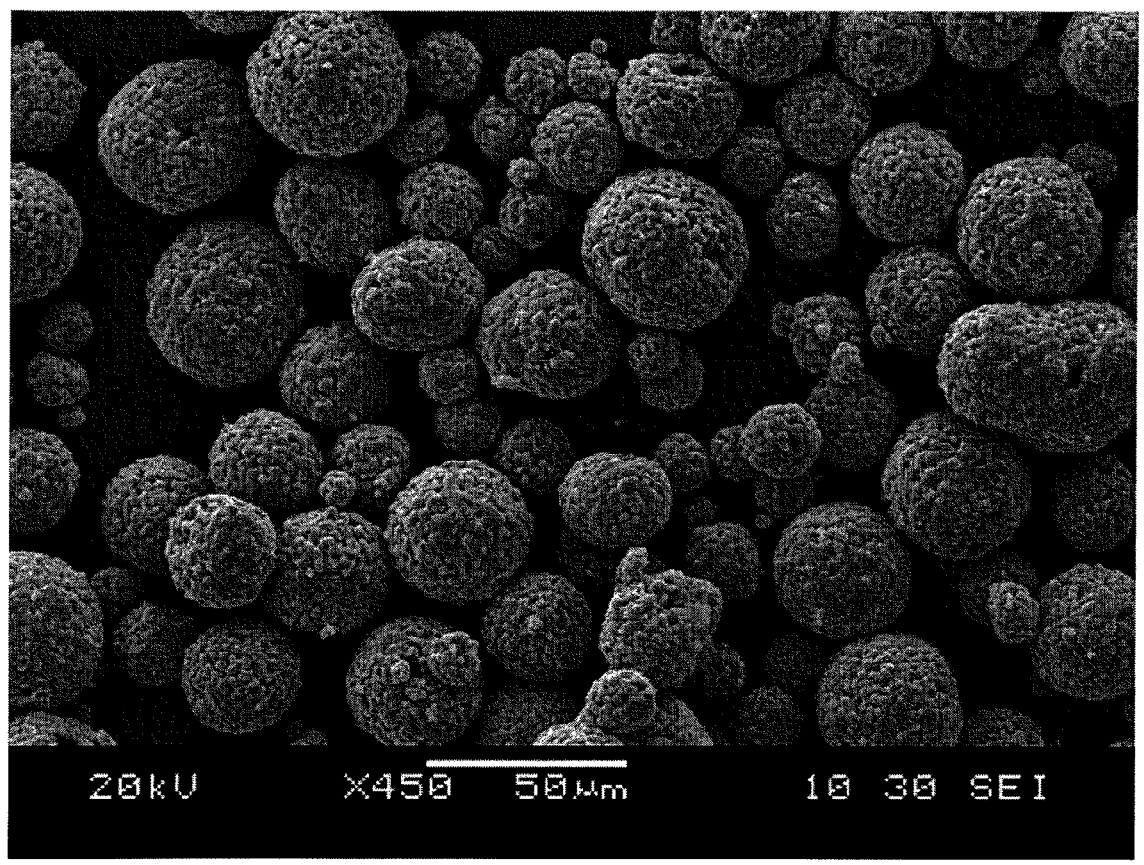
FIG. 6 is an observed image (with magnification of 450 times) of particles of a core material for an electrophotographic ferrite carrier (sample (B) in Example 2) by using a scanning electron microscope.

In contrast, the sample (B) was prepared, which had the same volume median diameter ($D_{50}$) of 35 μm, but had a completely different specific surface area (0.28 m²/g) measured by a BET method. FIG. 6 shows an observation image (with magnification of 450 times) of the sample (B), which was obtained by using the scanning electron microscope. The sample (B) showed the value of 0.88 for $CPE-P_1$.

Figure 7:
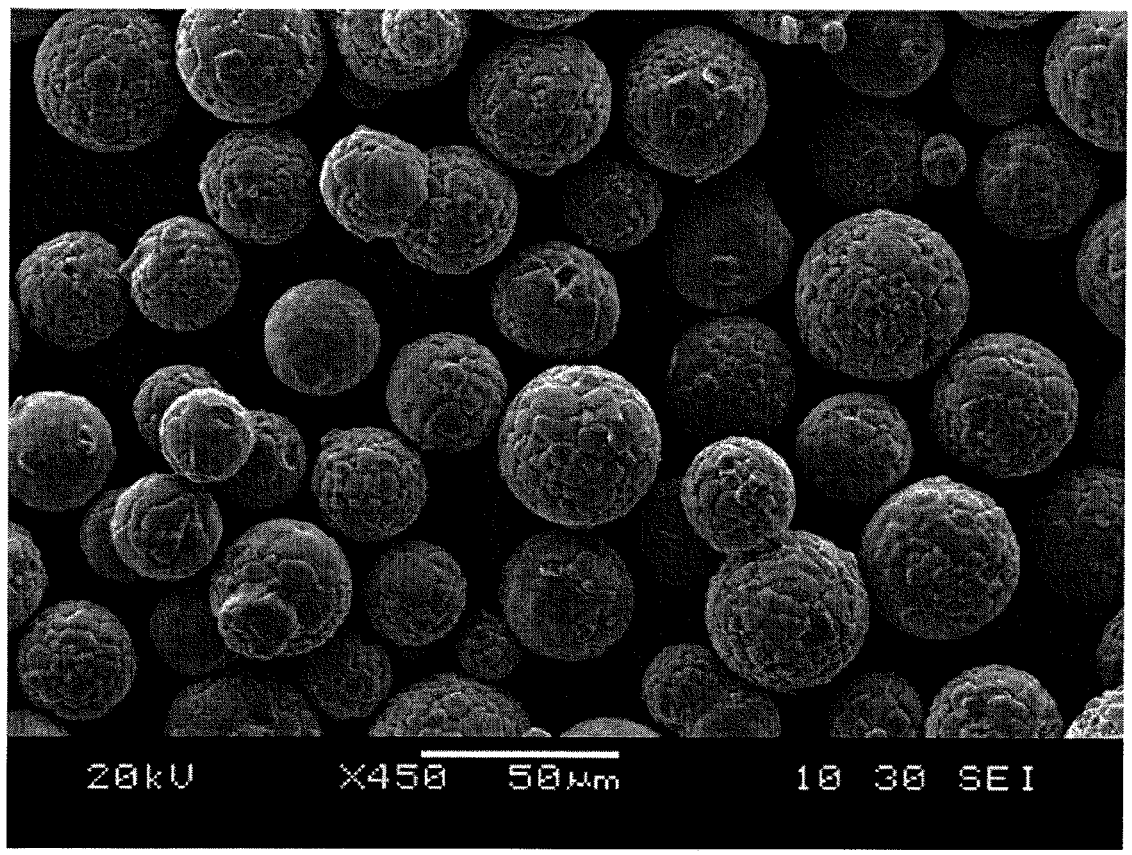
FIG. 7 is an observed image (with magnification of 450 times) of particles of a core material for an electrophotographic ferrite carrier (sample (C) in Example 2) by using a scanning electron microscope.

Furthermore, a sample (C) was prepared, which had the same volume median diameter ($D_{50}$) of 35 μm and had a specific surface area (0.07 m²/g) measured by a BET method that is an approximately similar value to that of the sample (A). FIG. 7 shows an observation image (with magnification of 450 times) of the sample (C), which was obtained by using the scanning electron microscope. The sample (C) showed the value of 0.96 for $CPE-P_1$.

In consideration of the description above, the sample (A) has the specific surface area measured by a BET method of 0.08 m²/g and the sample (B) has the specific surface area of 0.28 m²/g. So, the samples have a quite different specific surface area. However, for $CPE-P_1$, the sample (A) has the value of 0.88 and the sample (B) has the value of 0.89, which are extremely similar. It is because when the observation images of both samples through the scanning electron microscope (FIG. 5 and FIG. 6) are compared, both samples have approximately similar boundaries on particles which compose the core material for the electrophotographic ferrite carrier. Accordingly, a value of $CPE-P_1$ can be considered to show a state (irregularity state) of each particle of the core material for the electrophotographic ferrite carrier.

Furthermore, the sample (A) has the specific surface area measured by a BET method of 0.08 m²/g, and the sample (C) has the specific surface area of 0.07 m²/g, which are similar values. However, when values of $CPE\text{-}P_1$ are compared between the sample (A) and the sample (C), the sample (A) shows the value of 0.89 and the sample (C) shows the value of 0.96, they are quite different. It is because when the observation images of both samples obtained with the scanning electron microscope (FIG. 5 and FIG. 7) are compared, it is easily understood that both samples show completely different surface shape of respective particles of the core material for the electrophotographic ferrite carrier. Specifically, it can be clearly announced that the value of $CPE\text{-}P_1$ can indicate the state of each particle of the core material for the electrophotographic ferrite carrier, which the specific surface area measured by a BET method could never indicate.

INDUSTRIAL APPLICABILITY

A method for inspecting the quality of a core material for an electrophotographic ferrite carrier according to the present invention using an AC-resistance measuring method can obtain various AC-resistance values which can be substituted with conventional parameters for powder characteristics. As a result, the measurement method enables to gather information on the state of each particle of a core material for the electrophotographic ferrite carrier and the state of the particles as the powder simultaneously and separately. Accordingly, the measurement method also enables to gather a plurality of such information for judging the state of each particle and the state of the particles as the powder independently in one operation of analysis. Consequently, the measurement method has advantages in eliminating the requirements for using a plurality of analyzers and/or inspectors for measuring a plurality of powder characteristics.

What is claimed is:

1. A method for inspecting a quality of a core material for an electrophotographic ferrite carrier, comprising:
    measuring electrical impedances of the core material for the electrophotographic ferrite carrier in a frequency range to obtain a Cole-Cole plot in which a real part of each measured impedance is arranged in an X-axis and an imaginary part of each measured impedance is arranged in a Y-axis; and
    evaluating an average surface shape of particles of the core material for the electrophotographic ferrite carrier using the Cole-Cole plot and an equivalent circuit model to which the measured impedances are applied.

2. The method for inspecting a quality of a core material for the electrophotographic ferrite carrier according to claim 1, wherein the Cole-Cole plot is obtained by changing the frequency of a current applied in the impedance measurement in a frequency range of 0.01 Hz to 1 MHz.

3. The method for inspecting a quality of a core material for the electrophotographic ferrite carrier according to claim 1, wherein a state of the particles of the core material for the electrophotographic ferrite carrier is evaluated by using a parameter obtained from the Cole-Cole plot.

4. The method for inspecting a quality of a core material for the electrophotographic ferrite carrier according to claim 1, wherein the quality of the core material for the electrophotographic ferrite carrier is judged by fitting an equivalent circuit model to the Cole-Cole plot and evaluating the quality of the core material based on parameters of the equivalent circuit model, the parameters including a parameter for evaluating a state of the particles of the core material for the electrophotographic ferrite carrier.

5. The method for inspecting a quality of a core material for the electrophotographic ferrite carrier according to claim 1, wherein the quality of the core material for the electrophotographic ferrite carrier is judged by using a relationship between a time constant $T_1$ which indicates a state of the particles and a time constant $T_2$ which indicates a state of a powder comprising the particles, the time constants $T_1$ and $T_2$ being obtained from the Cole-Cole plot.

6. A method for inspecting a quality of a core material of an electrophotographic ferrite carrier, comprising:
    performing electrical impedance measurements of the core material in a frequency range to obtain measurement data;
    determining parameters of an equivalent circuit model by fitting the equivalent circuit model to the measurement data; and
    evaluating the quality of the core material based on the determined parameters, wherein one of the parameters of the equivalent circuit model is correlated with a specific surface area of particles of the core material, and at least one of the parameters of the equivalent circuit model is correlated with a volume median diameter of particles of the core material.

* * * * *